(12) United States Patent
Badcott et al.

(10) Patent No.: US 11,583,308 B2
(45) Date of Patent: Feb. 21, 2023

(54) TORSIONAL ULTRASOUND GENERATOR FOR ORTHOPAEDIC PROCEDURES

(71) Applicant: RADLEY SCIENTIFIC LIMITED, Ashburton (GB)

(72) Inventors: Sean Martin Badcott, Paignton (GB); Stephen Michael Radley Young, Newton Abbot (GB); Michael John Radley Young, Ashburton (GB)

(73) Assignee: Radley Scientific Limited

( * ) Notice: Subject to any disclaimer, the term of this patent is extended or adjusted under 35 U.S.C. 154(b) by 445 days.

(21) Appl. No.: 16/478,429

(22) PCT Filed: Jan. 17, 2018

(86) PCT No.: PCT/GB2018/000009
§ 371 (c)(1),
(2) Date: Jul. 16, 2019

(87) PCT Pub. No.: WO2018/134556
PCT Pub. Date: Jul. 26, 2018

(65) Prior Publication Data
US 2019/0365409 A1 Dec. 5, 2019

(30) Foreign Application Priority Data
Jan. 17, 2017 (GB) ...................................... 1700826

(51) Int. Cl.
*A61B 17/32* (2006.01)
(52) U.S. Cl.
CPC ................ *A61B 17/320068* (2013.01); *A61B 2017/320098* (2017.08)
(58) Field of Classification Search
CPC ............ A61B 17/320068; A61B 2017/320098
See application file for complete search history.

(56) References Cited

U.S. PATENT DOCUMENTS

| 8,836,200 | B2 * | 9/2014 | Young | A61B 17/320068 |
| | | | | 310/323.02 |
| 10,137,033 | B2 * | 11/2018 | Clayton | G06F 30/23 |
| 2013/0184711 | A1 | 7/2013 | Rad | |

FOREIGN PATENT DOCUMENTS

WO 9944514 A1 9/1999

OTHER PUBLICATIONS

International Search Report and Written Opinion issued in PCT/GB2018/000009 dated Apr. 26, 2018.

* cited by examiner

*Primary Examiner* — Julian W Woo
(74) *Attorney, Agent, or Firm* — Heslin Rothenberg Farley & Mesiti, P.C.

(57) ABSTRACT

Apparatus for generating torsional-mode ultrasonic vibrations, for example in a surgical tool, comprises an ultrasonic transducer that would conventionally produce longitudinal-mode ultrasonic vibrations, with a long, hollow, cylindrical, mode converter mounted coaxially to its distal end. A plurality of holes are formed through the walls of the mode converters. These holes are arranged in multiple parallel helical rows, extending along and around the cylindrical mode converters. Holes within the same row are spaced relatively closely, compared with the spacing between rows. Relationships have been established between the hole diameter (d), the spacing between rows (W), the spacing between holes in the same row (l), the spacing between individual holes in adjacent rows (L), and the overall diameter of the mode converter (D). In a preferred version, the holes through the walls of the second mode converter are tapered inwardly, rather than being cylindrical holes as in the first mode converter.

19 Claims, 4 Drawing Sheets

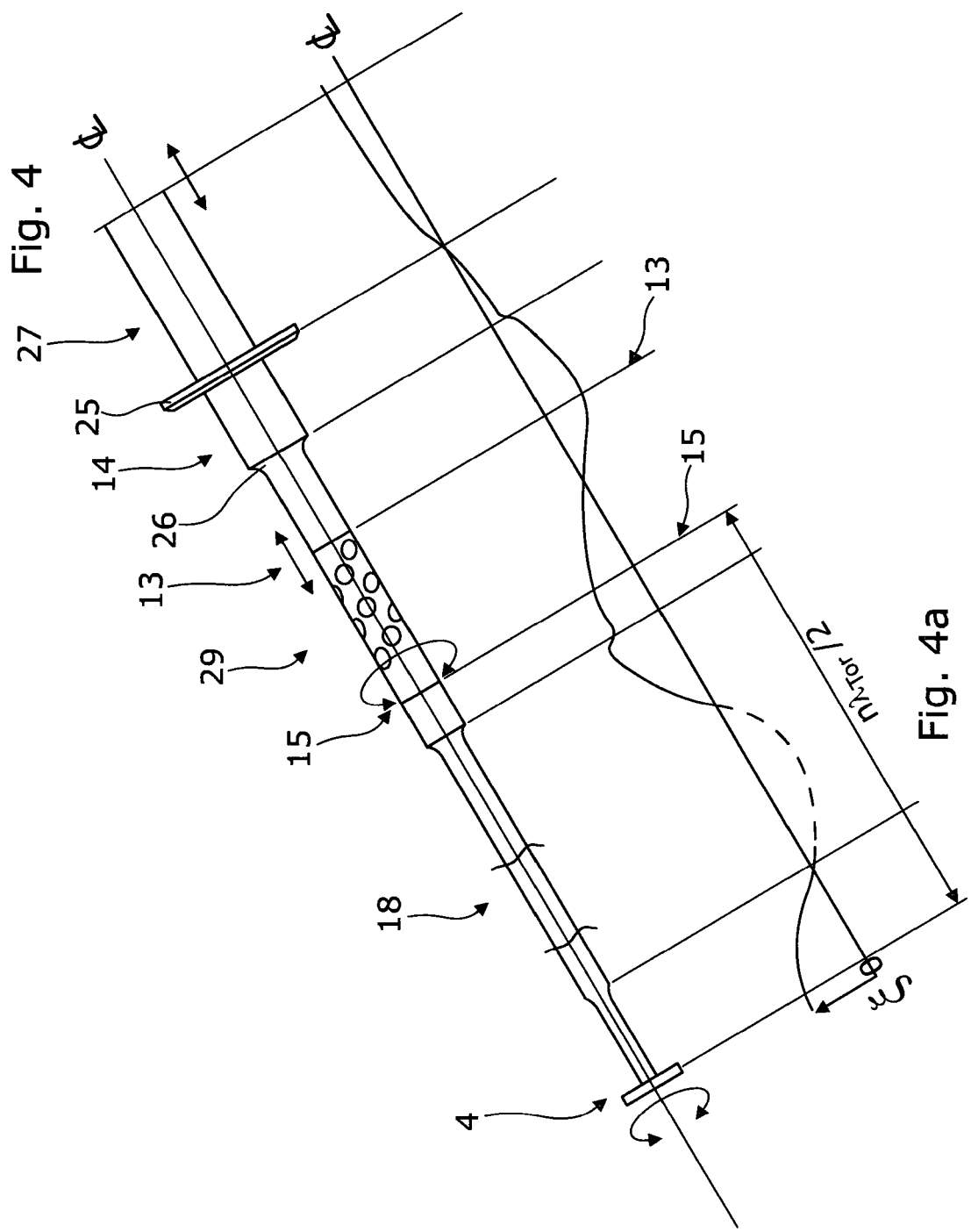

TORSIONAL ULTRASOUND GENERATOR FOR ORTHOPAEDIC PROCEDURES

CROSS REFERENCE TO RELATED APPLICATIONS

This application is a U.S. National Phase filing under 35 U.S.C. § 371 of International Application PCT/GB2018/000009, filed Jan. 17, 2018, and published as WO 2018/134556 A1 on Jul. 26, 2018. PCT/GB2018/000009 claims priority from British application number 1700826.9, filed Jan. 17, 2017. The entire contents of each of these prior applications are hereby incorporated herein by reference.

The present invention relates to apparatus for generating torsional-mode ultrasonic vibrations for activating an ultrasonically-vibratable tool, such as a surgical tool. More particularly but not exclusively, it relates to apparatus for generating torsional-mode ultrasonic vibrations, adapted to be incorporated into a hand piece of a surgical tool, especially a surgical tool for orthopaedic procedures.

It is known to use torsional-mode ultrasound in advanced orthopaedic revision instruments, and for specialist trauma implant removal. The design of apparatus employing torsional-mode vibrations offers enhanced safety with a greatly reduced risk of damaging fenestration of bone, relative to earlier techniques using longitudinal-mode ultrasonic vibrations or even impact-driven cutting tools (see Young et al in International Patent Application No. WO2015/198005 and U.S. Pat. No. 8,836,200). In some cases, a protective shroud is needed around the waveguide that links the ultrasound-generating transducer to the end-effector of the tool. However, where the tool can safely be deployed without such a shroud, the efficiency of the oscillatory system can be significantly improved by using combined longitudinal and torsional modes. Several examples of techniques to achieve this are known, such as those disclosed by Wuchinich et al in U.S. Patent Application No. US2001/0047166, Boukhny et al in U.S. Patent Application No. US2005/0277869 and Easley et al in U.S. Patent Application No. US2006/0004396. In each example, the essential physical feature to create proportional mode conversion from longitudinal to torsional mode, a cross-sectional inhomogeneity, involves machining helical grooves in selected regions of the waveguide or horn of the tool. Machining these features in the titanium alloy of the tool, in order to create acoustically efficient systems, is difficult, however, which has limited the use of this technology.

The object of the present invention is hence to provide apparatus to produce torsional-mode ultrasonic vibrations, particularly apparatus suitable to energise ultrasonically-activatable orthopaedic surgical tools, that obviates the drawbacks of existing systems but provides comparable benefits as discussed above.

According to a first aspect of the present invention, there is provided apparatus adapted to produce torsional-mode ultrasonic vibrations, comprising a coaxially-aligned array of piezo-electric ceramic elements having a hollow elongate conversion element extending from a distal end of the array, wherein a plurality of holes extend through a wall of the hollow elongate conversion element, said plurality of holes being so arranged as to form one or more rows of holes, wherein the or each row of holes extends helically along and around the conversion element.

Preferably, each said hole is identical to each other said hole.

Advantageously, each said hole has a centreline that intersects with a longitudinal centreline of the hollow elongate conversion element.

Preferably, there are a plurality of said rows of holes extending helically about the conversion element.

Advantageously, each said row of holes extends in parallel to each other row of holes.

Each said row of holes may be spaced by a constant distance from each other said row of holes.

Preferably, each said hole tapes towards an interior of the hollows elongate conversion element.

Advantageously, each said hole is then conical or frustoconical.

Alternatively, each said hole is cylindrical.

Alternatively, each said hole has an elliptical cross-section.

Alternatively, each said hole has a generally square cross-section.

Preferably, the hollow elongate conversion element is cylindrical.

Advantageously, a hollow interior of the elongate conversion element comprises an elongate lumen extending along a longitudinal axis of the elongate conversion element.

The hollow elongate conversion element may have a constant cross-sectional profile along its length.

The hollow elongate conversion element may have wall means having a constant thickness throughout.

Preferably, a first ratio of an external diameter of the conversion element (D) to an effective separation of adjacent rows of holes (W−d) is greater than 4:1.

Advantageously, the first ratio of an external diameter of the conversion element (D) to an effective separation of adjacent rows of holes (W−d) is greater than 6:1.

The first ratio of an external diameter of the conversion element (D) to an effective separation of adjacent rows of holes (W−d) is advantageously less than 15:1.

The first ratio of an external diameter of the conversion element (D) to an effective separation of adjacent rows of holes (W−d) may be less than 10:1.

Preferably, a second ratio of an effective separation of adjacent rows of holes (W−d) to a distance between holes in the same row l is greater than 1.5:1.

Advantageously, a second ratio of an effective separation of adjacent rows of holes (W−d) to a distance between holes in the same row l is greater than 1.7:1.

A second ratio of an effective separation of adjacent rows of holes (W−d) to a distance between holes in the same row l is advantageously less than 5:1.

A second ratio of an effective separation of adjacent rows of holes (W−d) to a distance between holes in the same row l may be less than 3.75:1.

According to a second aspect of the present invention, there is provided a surgical tool activated by torsional-mode ultrasonic vibrations, comprising apparatus as described in the first aspect above, with elongate waveguide means adapted to transmit ultrasonic vibrations extending coaxially from a distal end of the hollow elongate conversions element, and an effector element of the surgical tool located to or adjacent a distal end of the waveguide means.

Embodiments of the present inventions will now be more particularly described by way of example and with reference to the figures of the accompanying drawings, in which:

FIG. 4 is a side elevation of the surgical tool of FIG. 2;

FIG. 4a is a graph of the displacement amplitude of the torsional vibrations along a length of the surgical tool, aligned with FIG. 4;

Figure 1:
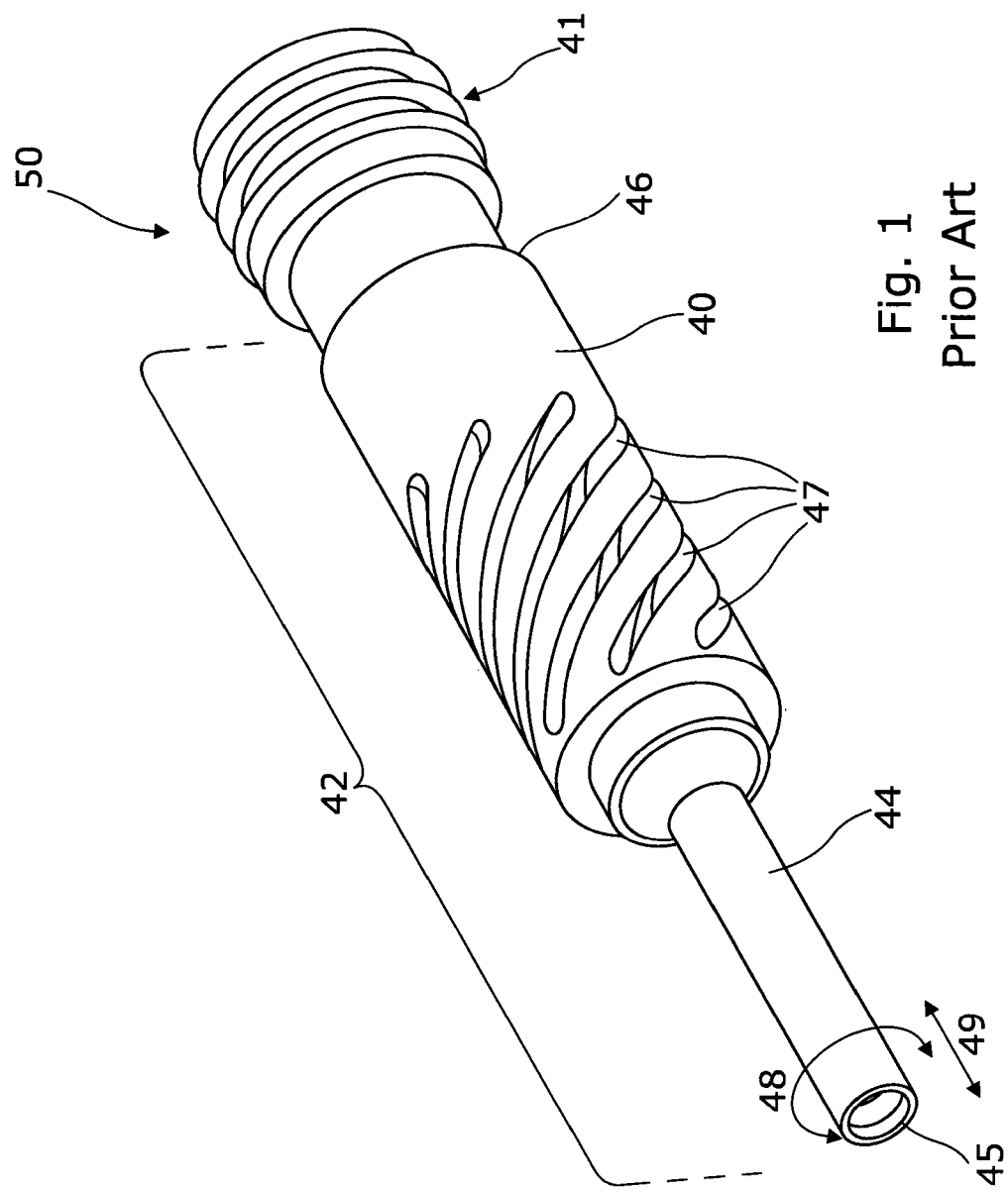
FIG. 1 is a perspective view of known apparatus for producing torsional-mode ultrasonic vibrations.

Referring now to the Figures and to FIG. 1 in particular, there is shown a known apparatus 50 for producing torsional-mode ultrasonic vibrations, specifically that disclosed in US2005/0277869 by Boukhny. This comprises a transducer 41 of conventional form comprising a stack of PZT ceramic rings, connected to a stepped conversion horn 42 at a proximal end 46 of the horn 42. The transducer 41 is adapted to produce longitudinal-mode ultrasonic vibrations when a suitable electrical signal is applied, via electrodes interleaved between the PZT rings of the stack. The converter horn 42 comprises a first proximal portion 40 one-quarter wavelength long, into which a series of parallel helical grooves 47 have been cut, and a plain second distal portion 44 of lesser diameter, also one-quarter wavelength long, terminating at a distal end 45 of the horn 42. At this distal end 45, the displacement of ultrasonic vibrations generated by the transducer 41 and transmitted through the converter horn 42 has become a combination of torsional and longitudinal modes, as represented by arrows 48 and 49 respectively.

This example of the prior art demonstrates how, in an axially/longitudinally excited rod system, in which a section of rod one-quarter wavelength long has been machined with a series of parallel helical grooves, conversion of longitudinal to torsional vibrations occurs. However, the spacing and depth of these grooves critically affects the proportions of torsional to longitudinal mode displacement produced. (It should be noted that the apparatus shown in FIG. 1 is believed to have the disadvantages of known systems discussed in the introductory passages above). Cutting such helical grooves accurately has been found to be a difficult process, such apparatus 50 being composed mainly of titanium, in most cases.

Figure 2:
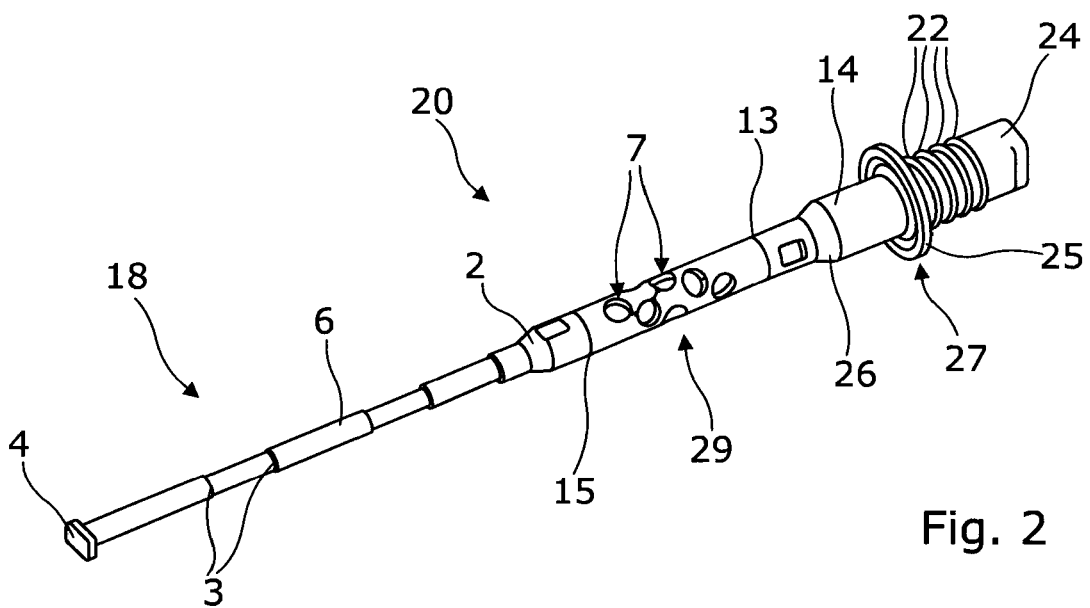
FIG. 2 is a perspective view of a surgical tool comprising apparatus for producing torsional-mode ultrasonic vibrations embodying the present invention.

In FIG. 2, an alternative oscillatory rod system is illustrated, embodying the present invention and providing an improved means of converting longitudinal-mode ultrasonic vibrations partially or wholly to torsional-mode vibrations. This system is embodied in a surgical tool 20, comprising a transducer 27, a first hollow-section mode converter 29, and an instrument designed for the removal of orthopaedic bone cement 18. The transducer 27 here is of a conventional axial mode Langevin transducer design, consisting of a plurality of piezoelectric ceramic (PZT) rings 22, coaxially arranged, interleaved with annular electrodes, and sandwiched between a back plate 24 and a front plate 14. The front plate 14 is shown with an optional step 26 to create appropriate vibrational motion characteristics at its distal/output end 13 (see below for details). An isolation flange 25 is optionally located between the front plate 14 and the transducer stack 22, at a nodal point of the ultrasonic vibrations generated therein. The isolation flange 25 allows a casing of a handpiece to be mounted around the transducer 22 and the first mode converter 29, isolated from the ultrasonic vibrations.

The distal end 13 of the transducer 27 is attached by a threaded mounting (not visible) to the first hollow-section mode converter 29, (shown in more detail in FIG. 3 below). The first mode converter 29 is provided with a plurality of radially-drilled holes 11 arranged in a series of parallelly-extending helices 7, each hole 11 being drilled wholly through a wall of the first hollow mode converter 29 into its interior (again, shown in full in FIG. 3 below).

To the distal end 15 of the first mode converter 29 is attached the instrument for the removal of orthopaedic bone cement 18, again by means of a threaded mounting. The representative bone cement removal instrument 18 illustrated comprises a proximal section 2 of enlarged diameter, an elongate waveguide portion 6 and an end effector 4 at the distal end of the waveguide portion 6. Stepped section changes 3 are optionally present within the waveguide portion 6; these may facilitate frequency tuning of the system 20 without affecting the vibrational mode therein.

Figure 3:
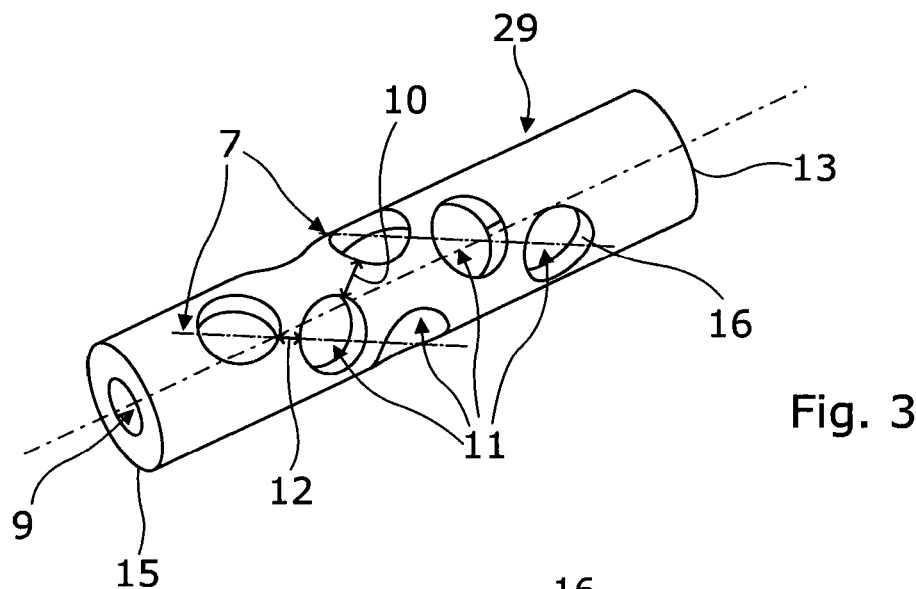
FIG. 3 is a perspective view of a first conversion element isolated from the apparatus of FIG. 2.
Figure 3A:
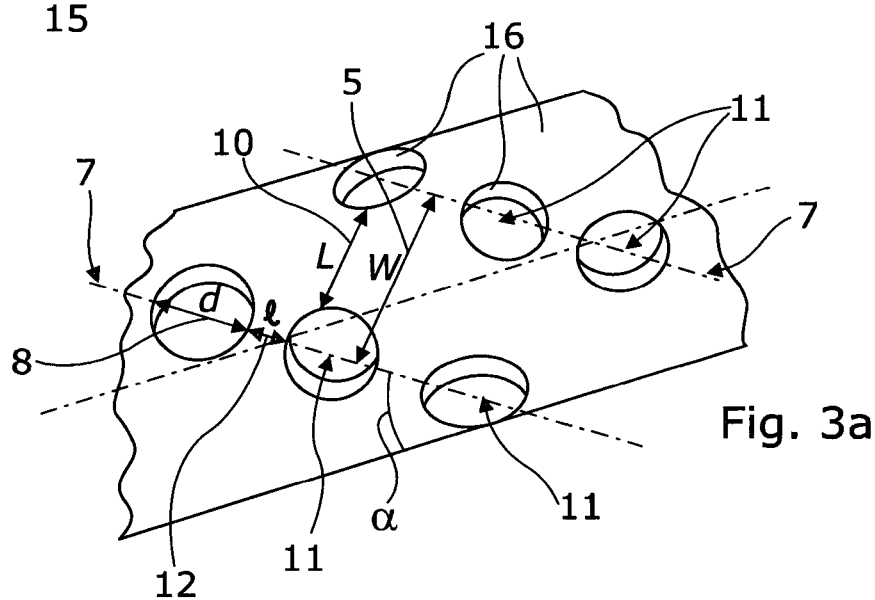
FIG. 3a is an enlarged scrap perspective view of a portion of the first conversion element of FIG. 3.

FIGS. 3 and 3a show more details of the first hollow mode converter 29. The body of the first mode converter 29 is cylindrical, with a hollow centre 9 extending longitudinally along a centreline of the first mode converter 29. Thus, the walls 16 of the first mode converter 29 have a constant thickness. The plurality of identical circular-section holes 11 each extend through the wall 16 into the hollow centre 9, with a central axis of each hole 11 intersecting with a longitudinal axis of the first mode converter 29.

The holes 11 are all arranged in a series of parallel rows, lines or chains 7, each row 7 extending helically around the first mode converter 29, in parallel with each other row 7.

FIG. 3 shows details of critical dimensions of the holes 11, the rows 7 and the first mode converter 29 which are believed to determine the degree of vibrational mode conversion, and so the proportion of torsional mode vibrations transmitted at the distal end 15 into the cement removal instrument 18. Two parallel rows 7 of holes 11 are shown in these Figures, each having three holes 11 of the row 7 visible. Four critical dimensions are shown: W (5), d (8), L (10) and l (12). W represents the constant distance (measured centre line to centre line) between adjacent parallel rows 7 of holes 11; d represents the identical diameter of each hole 11; L represents the shortest distance separating holes 11 in adjacent helical rows 7, measured rim to rim; and l represents the constant distance between adjacent holes 11 in the same row 7. The angle α defines the spiral angle of each helical row 7 relative to the longitudinal axis of the first mode converter 29. D (not labelled in this Figure) is the outer diameter of the cylindrical first mode converter 29.

The defining relationship between the critical dimensions, which determines the mode composition, is set out in the following expressions. Significant torsional mode conversion occurs when:

$$W-d \geq l$$

and when the spiral angle α lies within the range:

$$60° > \alpha > 45°.$$

(NB: The quantities (W−d) and L are not the same. Since the holes 11 in adjacent rows 7 are not necessarily aligned, L, the closest approach of two individual holes 11, will be greater than or equal to (W−d)).

Additionally, initial work suggested that:

$$5 > 2\pi D/L > 2;$$

$$5 > 2\pi D/(W-d) > 2;$$

$$3 > (W-d)/l > 1$$

although further developments have indicated that for best results:

$$15 > D/(W-d) > 4,$$

and preferably $$10 > D/(W-d) > 6;$$

while $$5 > (W-d)/l > 1.5,$$

and preferably $$3.75 > (W-d)/l > 1.7.$$

FIGS. 4 and 4a show schematically the mode changes along a length of the system 20 in relation to the displacement amplitude ξ defining nodes and antinodes in each of the three main elements 27, 29, 18. The system 20 illustrated shows a purely torsional output from the mode converter 29 and throughout the cement removal instrument 18. The removal instrument 18 ideally has a length of nλ/2, where λ is the wavelength of the ultrasonic vibrations, here torsional-mode.

Figure 5A:
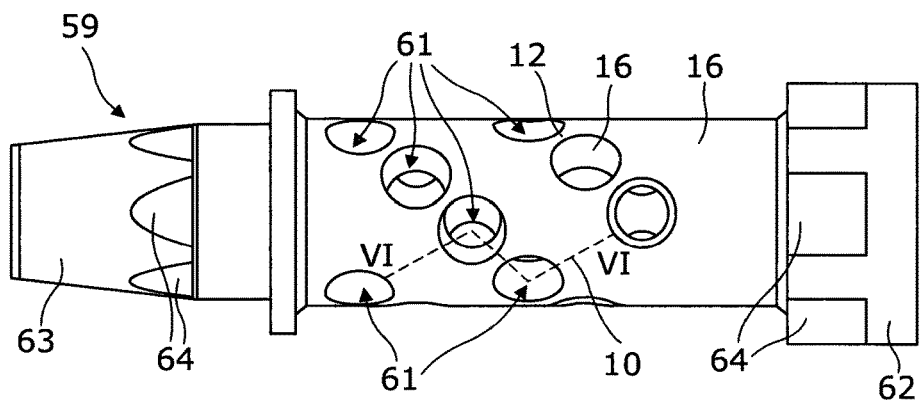
FIGS. 5a and 5b are side elevations of a second conversion element embodying the present invention.
Figure 5B:
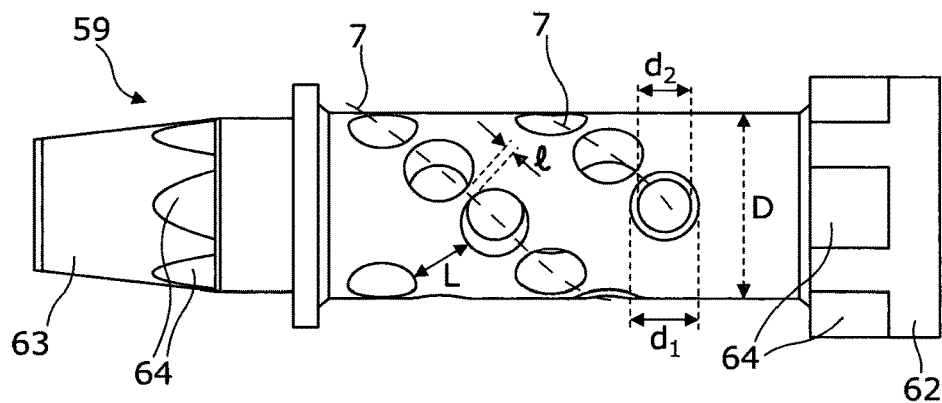

FIGS. 5a and 5b show a second hollow-section mode converter 59, which can be incorporated into a surgical tool 20, in preference to the first mode converter 29. The second mode converter 59 is shown twice to simplify labelling. Also, in FIG. 5b, features on the far wall 16 of the second mode converter 59, which are visible through holes 61 in the near wall 16 in FIG. 5a, are omitted for clarity.

The first 29 and second 59 mode converters are functionally and structurally very similar; the major difference between them lies in the profile of the holes 61 drilled through the wall 16 of the second mode converter 59. The arrangement of these holes 61 in helically-extending rows 7 remains the same. The holes 11 of the first mode converter 29 are cylindrical in profile, but the holes 61 of the second mode converter 59 are frusto-conical in profile, tapering towards the hollow interior 9 of the second mode converter 59. The cone angle β subtended by each hole 61 is typically about 14° (see FIG. 6 below). The second mode converter 59 is shown with connecting elements 62, 63 at each end; each provided with spanner flats 64 for tightening the threaded connections used.

Figure 6:
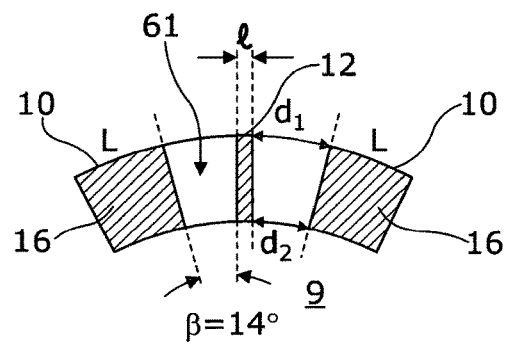
FIG. 6 is a schematic scrap cross-section of a wall of the second conversion element of FIGS. 5a and 5b, taken along dotted line VI-VI.

FIG. 6 shows a scrap cross-section through the wall 16 of the second mode converter 59, following the zig-zag line VI-VI in FIG. 5a so as to show the wall 16 profile between adjacent holes 61 in the same row 7 of holes 61 and between holes 61 in adjacent rows 7. The holes 61 are tapered towards the interior 9 of the second mode converter 59, with a cone angle β of 14° in this example. As a result, the thickness of the wall 16 between two adjacent holes 61 in the same row 7 is constant, equal to l, the distance between them across an outer surface of the second mode converter 59. If cylindrical holes 11 were used, the wall 16 between them would be much thinner towards the interior 9 of the mode converter 29, or the cylindrical holes 11 might even intersect at their inner ends. The tapered holes 61 themselves lessen in diameter from $d_1$ at the outer surface to $d_2$ as they enter the interior 9. Where a value for the hole diameter d is required, either $d_1$ or the mean value of $d_1$ and $d_2$ can be used, without it making a major difference. The portions of the wall 16 between holes 61 in adjacent rows 7 are still not of constant thickness, as can be seen in FIG. 6, but again the proportional variation makes far less difference than would variation in the narrow wall 16 between adjacent holes 61 in the same row 7.

Thus, the present invention recognises that the oscillatory characteristics of a series of helical grooves cut longitudinally into a cylindrical rod can be replicated or simulated by machining a variety of shapes to alter the cross-sectional stiffness, thereby encouraging displacement to occur in selected directions relative to the longitudinal axis of the rod. By selecting a tubular rod section and drilling a series of holes through the tube walls, arranged in a parallel helical configuration about the longitudinal axis of the tubular rod, two components of motion can be created downstream of the feature, when energised by a proximally-applied compression wave (longitudinal mode) input. Cylindrical drilled holes have been shown in FIGS. 2 to 3a above since they are the easiest shapes to manufacture. Tapered drilled holes (as in FIGS. 4 to 5) are also straightforward to produce with an appropriately profiled bit. However, by resorting to spark erosion techniques, other shapes could be generated as individual holes e.g. square or elliptical. Each of these would still be more easily formed than the existing elongate continuous spiral grooves of known converters, which the present invention is intended to replace.

The invention claimed is:

1. Apparatus adapted to produce torsional-mode ultrasonic vibrations, comprising a coaxially-aligned array of piezo-electric ceramic elements having a proximal end and a distal end, and a hollow elongate conversion element extending from the distal end of the coaxially-aligned array, the hollow elongate conversion element being defined by a wall, wherein a plurality of identical holes extend through said wall of the hollow elongate conversion element, said plurality of identical holes being so arranged as to form one or more rows of identical holes, wherein the or each said row of identical holes extends helically along and around the hollow elongate conversion element.

2. Apparatus as claimed in claim 1 wherein the hollow elongate conversion element defines a longitudinal axis and a central axis defined by each hole of the plurality of identical holes intersects with the longitudinal axis of the hollow elongate conversion element.

3. Apparatus as claimed in claim 1, wherein the hollow elongate conversion element comprises a plurality of rows of identical holes, each row of said plurality of rows of holes extending helically about the conversion element.

4. Apparatus as claimed in claim 3, wherein each row of said plurality of rows of identical holes extends in parallel to each other row of said plurality of rows of holes.

5. Apparatus as claimed in claim 3, wherein each row of said plurality of rows of identical holes is spaced apart by a constant distance from each adjacent row of said plurality of rows of identical holes.

6. Apparatus as claimed in claim 1, wherein each hole within a row of identical holes is spaced apart by a constant distance from adjacent holes within the same row of identical holes.

7. Apparatus as claimed in claim 1, wherein each hole is tapered towards an interior of the hollow elongate conversion element.

8. Apparatus as claimed in claim 1, wherein each hole is cylindrical.

9. Apparatus as claimed in claim 1, wherein the hollow elongate conversion element is cylindrical.

10. Apparatus as claimed in claim 9, wherein the wall of the hollow elongate conversion element has a constant thickness throughout.

11. Apparatus as claimed in claim 9, wherein the hollow elongate conversion element has a hollow interior comprising an elongate lumen extending along a longitudinal axis of the hollow elongate conversion element.

12. Apparatus as claimed in claim 11, wherein the hollow elongate conversion element has a constant cross-sectional profile along its length.

13. Apparatus as claimed in claim 1, wherein an external diameter of the hollow elongate conversion element is (D), a constant distance, measured center line to center line, between adjacent parallel rows of holes is W, an identical diameter of each hole is d, an effective separation between adjacent rows of holes is (W-d), and a first ratio of (D) to (W-d) is greater than 4:1.

14. Apparatus as claimed in claim 13, wherein said first ratio of (D) to (W-d) is less than 15:1.

15. Apparatus as claimed in claim 1, wherein a constant distance, measured center line to center line, between adjacent parallel rows of holes is W, an identical diameter of each hole is d, an effective separation between adjacent rows of holes is (W-d), a distance between holes in the same row is (l), and a second ratio of (W-d) to (l) is greater than 1.5:1.

16. Apparatus as claimed in claim 15, wherein said second ratio of (W-d) to (l) is less than 5:1.

17. A surgical tool activated by torsional-mode ultrasonic vibrations, comprising apparatus adapted to produce torsional-mode ultrasonic vibrations as claimed in claim 1, further comprising an elongate waveguide adapted to transmit ultrasonic vibrations having a proximal end and a distal end and extending coaxially from the distal end of the hollow elongate conversion element of the apparatus, and comprising an effector element of the surgical tool located at or adjacent the distal end of the elongate waveguide.

18. Apparatus adapted to produce torsional-mode ultrasonic vibrations, comprising a coaxially-aligned array of piezo-electric ceramic elements having a proximal end and a distal end, and a hollow elongate conversion element extending from the distal end of the coaxially-aligned array, the hollow elongate conversion element being defined by a wall, wherein a plurality of holes extend through said wall of the hollow elongate conversion element, said plurality of holes being so arranged as to form one or more rows of holes, wherein the or each said row of holes extends helically along and around the hollow elongate conversion element, wherein the hollow elongate conversion element comprises a plurality of rows of holes, each row of said plurality of rows of holes extending helically about the conversion element.

19. Apparatus adapted to produce torsional-mode ultrasonic vibrations, comprising a coaxially-aligned array of piezo-electric ceramic elements having a proximal end and a distal end, and a hollow elongate conversion element extending from the distal end of the coaxially-aligned array, the hollow elongate conversion element being defined by a wall, wherein a plurality of holes extend through said wall of the hollow elongate conversion element, said plurality of holes being so arranged as to form one or more rows of holes, wherein the or each said row of holes extends helically along and around the hollow elongate conversion element, wherein each hole is cylindrical.

* * * * *